(12) United States Patent
Wilson et al.

(10) Patent No.: US 11,109,898 B2
(45) Date of Patent: Sep. 7, 2021

(54) FIXATION SYSTEMS AND METHODS OF REPAIRING A PARS FRACTURE

(71) Applicant: K2M, Inc., Leesburg, VA (US)

(72) Inventors: Lester Wilson, Middlesex (GB); Brandon Moore, Leesburg, VA (US); Alex Artaki, Falls Church, VA (US)

(73) Assignee: K2M, Inc., Leesburg, VA (US)

( * ) Notice: Subject to any disclaimer, the term of this patent is extended or adjusted under 35 U.S.C. 154(b) by 38 days.

(21) Appl. No.: 16/004,737

(22) Filed: Jun. 11, 2018

(65) Prior Publication Data
US 2018/0353222 A1 Dec. 13, 2018

Related U.S. Application Data

(60) Provisional application No. 62/517,373, filed on Jun. 9, 2017.

(51) Int. Cl.
*A61B 17/70* (2006.01)
*A61B 17/17* (2006.01)
(Continued)

(52) U.S. Cl.
CPC ...... *A61B 17/7074* (2013.01); *A61B 17/1757* (2013.01); *A61B 17/3472* (2013.01);
(Continued)

(58) Field of Classification Search
CPC ....... A61B 17/70–7098; A61B 17/7062–7071; A61B 17/844; A61B 2017/564
See application file for complete search history.

(56) References Cited

U.S. PATENT DOCUMENTS 6,951,561 B2 * 10/2005 Warren ................... A61B 17/68
606/328
7,824,429 B2 * 11/2010 Culbert .............. A61B 17/7064
606/279
(Continued)

FOREIGN PATENT DOCUMENTS

EP 1850807 A2 11/2007

OTHER PUBLICATIONS

European Search Report dated Oct. 24, 2018 issued in corresponding EP Appln. No. 18176938.

*Primary Examiner* — Nicholas J Plionis
(74) *Attorney, Agent, or Firm* — Lerner, David, Littenberg, Krumholz & Mentlik, LLP

(57) ABSTRACT

A method of repairing a pars fracture includes docking a needle guide on a lamina of the pars, inserting a needle at least partially through the needle guide, inserting a stylet at least partially through the needle, inserting a guidewire at least partially through the needle, removing the needle from the needle guide, removing the needle guide, positioning a screw assembly in contact with the lamina and co-axially with the guidewire, rotating an elongated portion of the screw assembly with respect to the lamina to move the screw assembly distally with respect to the lamina such that a distal end of the elongated portion of the screw assembly travels through an interior portion of the pars and into a superior portion of the pars, and approximating the distal end of the elongated portion of the screw assembly and a collar of the screw assembly to approximate the interior portion of the pars and the superior portion of the pars.

10 Claims, 17 Drawing Sheets

(51) Int. Cl.
  *A61B 17/34* (2006.01)
  *A61B 17/86* (2006.01)
  *C07D 471/04* (2006.01)
  *C07D 471/14* (2006.01)
  *C07D 498/14* (2006.01)
  *A61B 17/56* (2006.01)
  *A61B 90/00* (2016.01)

(52) U.S. Cl.
  CPC ...... *A61B 17/7062* (2013.01); *A61B 17/7071* (2013.01); *A61B 17/864* (2013.01); *A61B 17/8685* (2013.01); *C07D 471/04* (2013.01); *C07D 471/14* (2013.01); *C07D 498/14* (2013.01); *A61B 2017/564* (2013.01); *A61B 2090/037* (2016.02)

(56) References Cited

U.S. PATENT DOCUMENTS

| | | | |
|---|---|---|---|
| 10,588,679 B2* | 3/2020 | Kukla | A61B 17/68 |
| 2006/0122610 A1 | 6/2006 | Culbert et al. | |
| 2007/0233146 A1 | 10/2007 | Henniges et al. | |
| 2008/0119849 A1* | 5/2008 | Beardsley | A61B 17/7032 606/306 |
| 2010/0312280 A1* | 12/2010 | Overes | A61B 17/68 606/264 |
| 2011/0202062 A1* | 8/2011 | O'Halloran | A61B 17/1671 606/92 |
| 2012/0029566 A1* | 2/2012 | Rezach | A61B 17/7041 606/264 |
| 2013/0226239 A1 | 8/2013 | Altarac et al. | |
| 2013/0268009 A1* | 10/2013 | Giordano | A61B 17/7059 606/280 |
| 2013/0325069 A1* | 12/2013 | Pereiro de Lamo | A61B 17/7032 606/263 |
| 2014/0378999 A1* | 12/2014 | Crawford | A61B 90/39 606/130 |
| 2015/0374416 A1* | 12/2015 | Warren | A61B 17/70 606/247 |
| 2016/0296254 A1* | 10/2016 | Dimar, II | A61B 17/7037 |
| 2017/0135706 A1* | 5/2017 | Frey | A61B 17/1703 |

* cited by examiner

SECTION 32-32

FIXATION SYSTEMS AND METHODS OF REPAIRING A PARS FRACTURE

CROSS-REFERENCE TO RELATED APPLICATION

The present application claims priority to, and the benefit of, U.S. Provisional Patent Application Ser. No. 62/517,373 filed on Jun. 9, 2017, the entire contents of which being herein incorporated by reference in its entirety.

TECHNICAL FIELD

The present disclosure relates generally to a fixation system, and more particularly, to fixation systems and methods of orthopedic surgery for repairing a pars fracture.

BACKGROUND

The spinal column is a complex system of bones and connective tissues that provides support for the human body and protection for the spinal cord and nerves. The adult spine includes an upper portion and a lower portion. The upper portion has twenty-four discrete bones, which are subdivided into three areas including seven cervical vertebrae, twelve thoracic vertebrae, and five lumbar vertebrae. The lower portion has the sacral and coccygeal bones. The vertebrae progressively increase in size from the upper portion downwards to the lower portion.

The vertebrae interlock with one another to form the spinal column. Each vertebra has a cylindrical bony body (i.e., vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as intervertebral discs.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies and is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury, which restrict the range of motion of the spine or interfere with important elements of the nervous system. The problems include, but are not limited to, scoliosis, kyphosis, excessive lordosis, spondylolisthesis, slipped or ruptured disc, degenerative disc disease, vertebral body fracture, tumors and pars interarticularis fracture. Persons suffering from any of the above conditions typically experience extreme and/or debilitating pain, and often times diminished nerve function. These conditions and their treatments can be further complicated if the patient is suffering from osteoporosis, or bone tissue thinning and loss of bone density.

There are many known spinal conditions, e.g., scoliosis, that require the imposition and/or maintenance of corrective forces on the spine in order to return the spine to its normal condition. As a result, numerous devices (e.g., alignment systems) have been developed for use in spinal fixation. However, it may be difficult to repair a fracture of a pars interarticularis (or a "pars fracture") since the damaged lamina may be challenging to access and due its undulating shape. Therefore, a need exists for a fixation system and method for repairing a pars fracture.

SUMMARY

The present disclosure relates to a method of repairing a pars fracture including docking a needle guide on a lamina of the pars, inserting a needle at least partially through the needle guide such that a distal end of the needle contacts the lamina, inserting a stylet at least partially through the needle such that a distal end of the stylet contacts the lamina, inserting a guidewire at least partially through the needle such that a distal end of the guidewire contacts the lamina, removing the needle from the needle guide, removing the needle guide, positioning a screw assembly in contact with the lamina and co-axially with the guidewire, rotating an elongated portion of the screw assembly with respect to the lamina to move the screw assembly distally with respect to the lamina such that a distal end of the elongated portion of the screw assembly travels through an interior portion of the pars and into a superior portion of the pars, and approximating the distal end of the elongated portion of the screw assembly and a collar of the screw assembly to approximate the interior portion of the pars and the superior portion of the pars.

In disclosed embodiments, the method also includes removing the guidewire through a channel of the elongated portion of the screw assembly. It is further disclosed that inserting the needle and inserting the stylet are performed at the same time.

Embodiments of the method also include severing a portion of the screw assembly after approximating the distal end of the elongated portion of the screw assembly with the collar of the screw assembly.

Further embodiments include engaging a surgical instrument with the screw assembly prior to approximating the distal end of the elongated portion of the screw assembly and the collar of the screw assembly, and may also include actuating a first movable handle of the surgical instrument to approximate the distal end of the elongated portion of the screw assembly and the collar of the screw assembly, and actuating a second movable handle of the surgical instrument to fix a longitudinal position of the collar of the screw assembly with respect to the elongated portion of the screw assembly.

It is also disclosed that the method includes removing the stylet from the needle.

The present disclosure also relates to a fixation system for repairing a pars fracture. The fixation system includes a needle guide, a needle, a guidewire, and a screw assembly. The needle guide is configured to be docked on a lamina of the pars. A portion of the needle is configured for insertion through a passage of the needle guide. A portion of the guidewire is configured for insertion through a passage of the needle. The screw assembly includes a collar and an elongated portion. The collar is movable with respect to the elongated portion. The screw assembly is configured to contact the lamina co-axially with the guidewire.

In disclosed embodiments, the fixation system also includes a surgical instrument configured to move the collar of the screw assembly with respect to the elongated portion of the screw assembly.

In embodiments of the fixation system, the elongated portion of the screw assembly includes a channel extending along its length. The channel is configured to accept at least a portion of the guidewire therethrough.

It is also disclosed that the fixation system includes a stylet. A portion of the stylet is configured for insertion through the passage of the needle.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Figure 1:
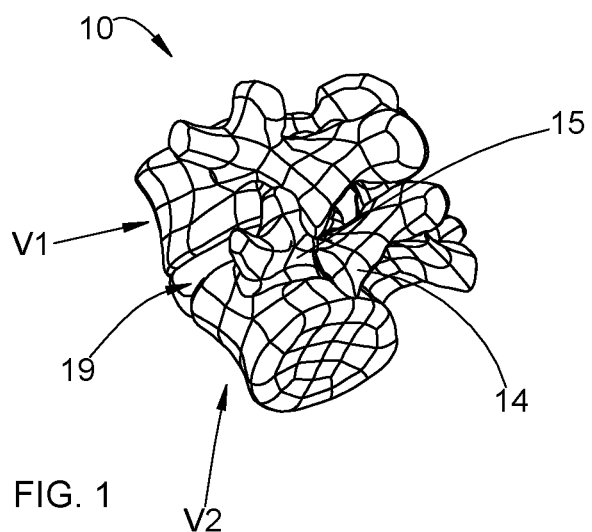
FIGS. 1 and 2 are perspective views of a fractured pars interarticularis.

Embodiments of the present disclosure are now described in detail with reference to the drawings in which like reference numerals designate identical or corresponding elements in each of the several views. As used herein, the term "clinician" refers to a doctor, nurse, or other care provider and may include support personnel. Throughout this description, the term "proximal" refers to a portion of a structure (e.g., a device or component thereof) closer to a clinician, while the term "distal" refers to a portion of the same structure further from the clinician. Additionally, in the drawings and in the description that follows, terms such as "upper," "lower," and similar directional terms are used simply for convenience of description and are not intended to limit the disclosure. In the following description, well-known functions or constructions are not described in detail to avoid obscuring the present disclosure in unnecessary detail.

Figure 2:
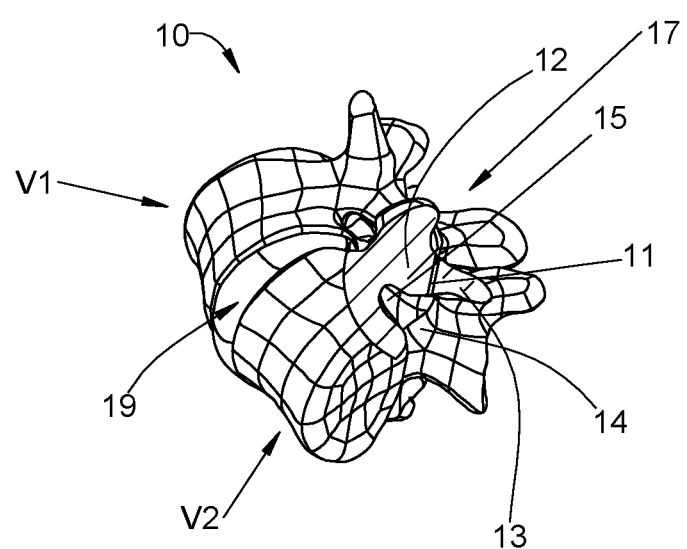

FIGS. 1 and 2 illustrate a portion of a patient's spine 10 having a first vertebra V1 and a second vertebra V2 that are separated by an intervertebral disc 19. This portion of a patient's spine 10 includes a pars interarticularis ("pars") having a crack or fracture 11 is shown between an interior portion 12 of the pars 17 and a superior portion 13 of the pars 17. The fracture 11 is on a portion of the lamina 14 that is positioned adjacent or near the pedicle 15. Due to the undulating shape of the lamina 14 and the location of the fracture 11, for instance, it is typically challenging to access and repair a pars fracture. The following description and corresponding figures describe a system and method of repairing the pars fracture.

A fixation system 100 for repairing a pars fracture is shown in the accompanying figures and generally includes a needle guide 200 (FIG. 5), a needle assembly 300 (FIG. 5), a stylet 400 (FIG. 5), a guidewire 500 (FIG. 9), a screw assembly 600 (FIG. 19), and a surgical instrument 700 (FIGS. 33-36) configured to engage a portion of the screw assembly 600.

Figure 3:
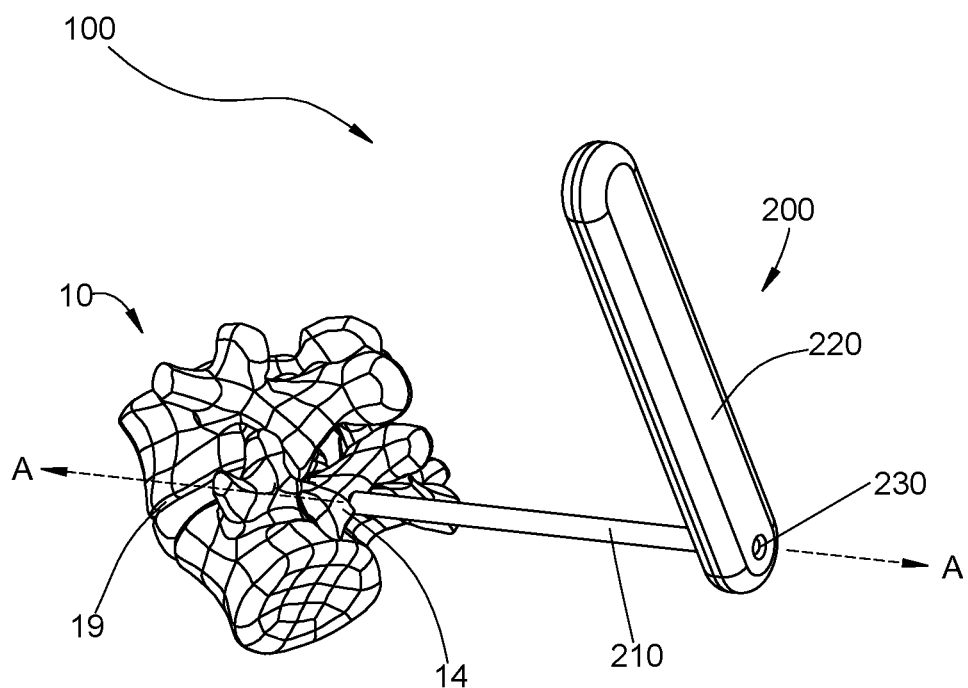
FIGS. 3 and 4 are perspective views of a needle guide docked on the lamina of the fractured pars interarticularis.
Figure 4:
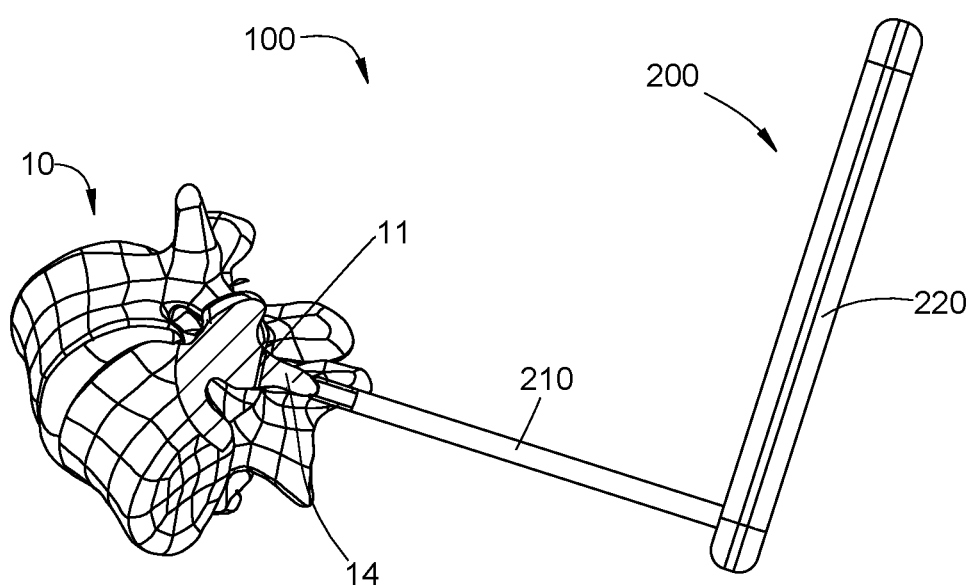

Referring to FIGS. 3 and 4, needle guide 200 of fixation system 100 is shown docked on the lamina 14. Needle guide 200 is positioned such that an axis "A" defined by an elongated portion 210 of needle guide 200 intersects the fracture 11. Elongated portion 210 extends distally from a handle portion 220 of needle guide 200. Needle guide 200 is docked on the lamina 14 using traditional methods. The needle guide 200 may also contain a self-aligning "divot" that allows the distal end of the needle guide 200 to "find" the crest of lamina and stay there during the insertion and removal of the subsequent instruments.

Figure 5:
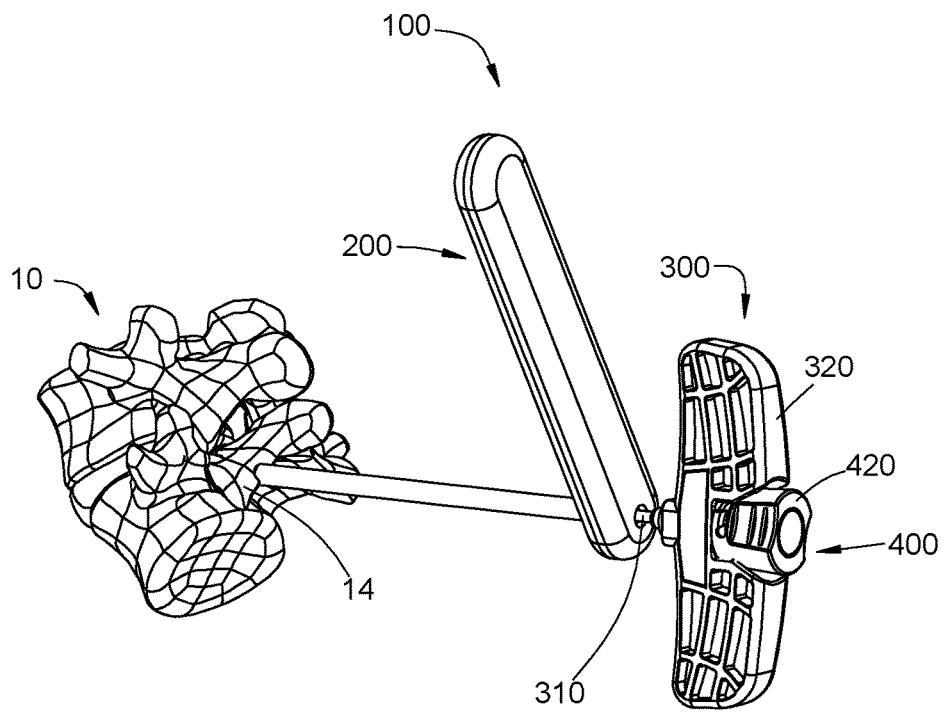
FIGS. 5 and 6 are perspective views of the needle guide shown in FIGS. 3 and 4 with a needle inserted therethrough.
Figure 6:
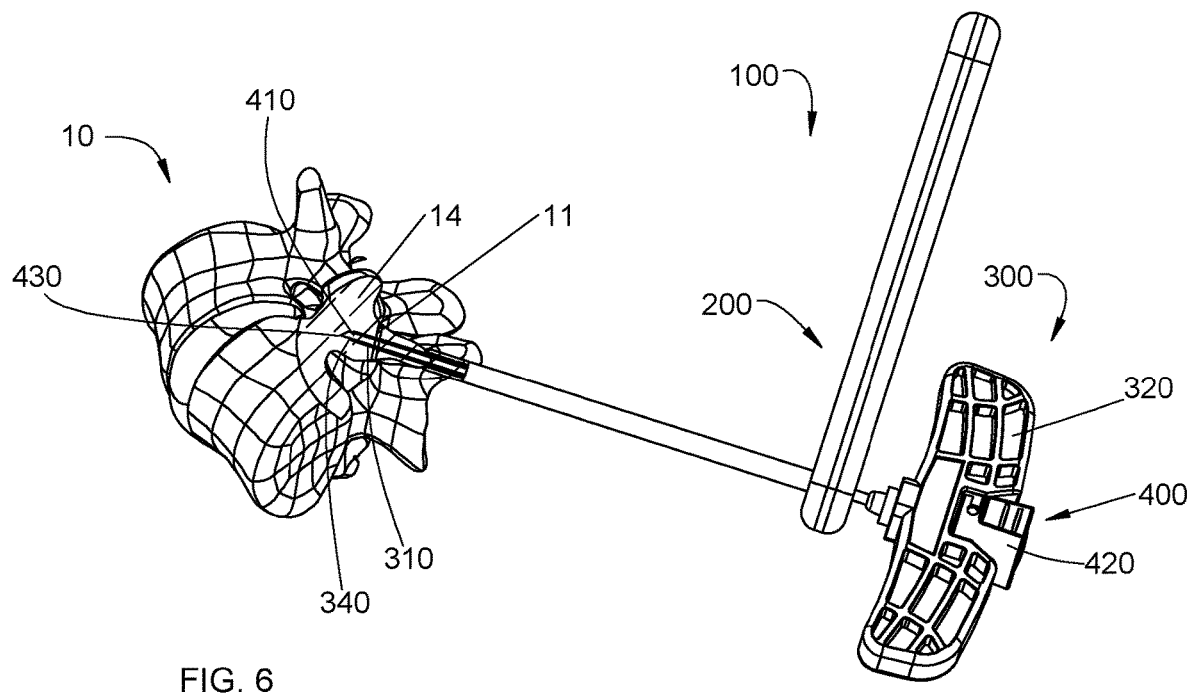
Figure 7:
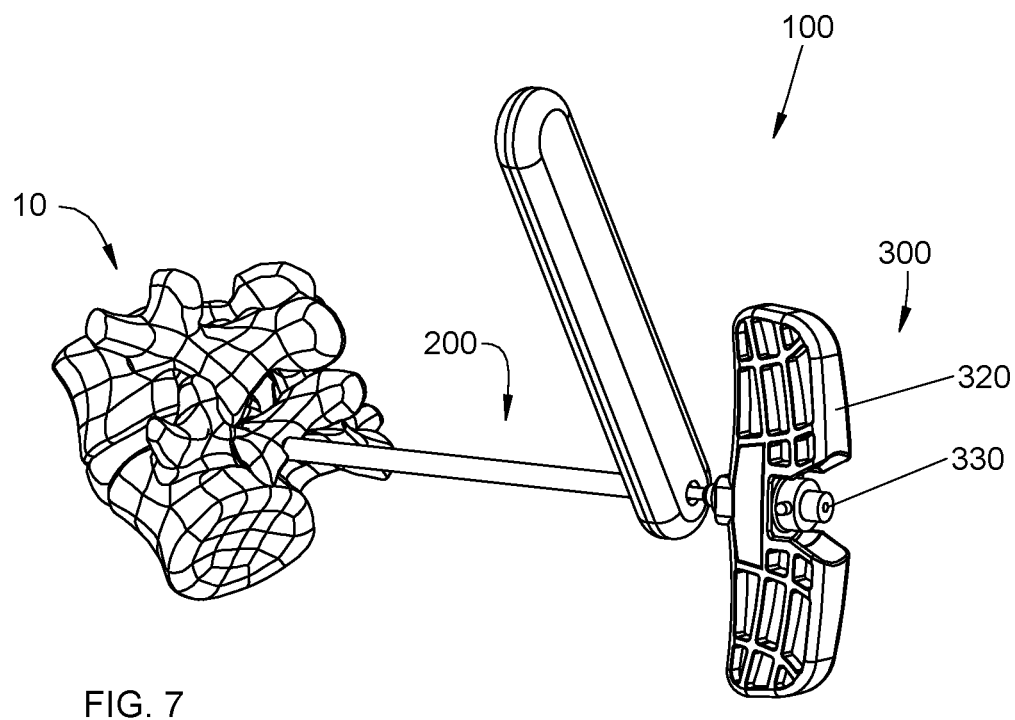
FIGS. 7 and 8 are perspective views of the needle guide and needle shown in FIGS. 5 and 6 with a stylet removed from the needle.

With reference to FIGS. 5 and 6, needle guide 200 remains docked on the lamina 14, and needle assembly 300 is shown. Needle assembly 300 includes an elongated portion 310 extending distally from a handle portion 320. Elongated portion 310 of needle assembly 300 defines a passage 330 extending therethrough (FIG. 7). Elongated portion 310 of needle assembly 300 is configured to be advanced through a passage 230 of needle guide 200 (FIG. 3).

With continued reference to FIGS. 5 and 6, stylet 400 is docked to needle assembly 300. An elongated portion 410 (FIG. 6) of stylet 400 extends distally from a handle portion 420 of stylet 400. Elongated portion 410 extends within passage 330 of needle assembly 300, and handle portion 420 of stylet 400 engages handle portion 320 of needle assembly 300. A distal tip 340 of needle assembly 300 engages the lamina 14, and a distal tip 430 of stylet 400 engages (e.g., penetrates) the lamina 14.

Figure 8:
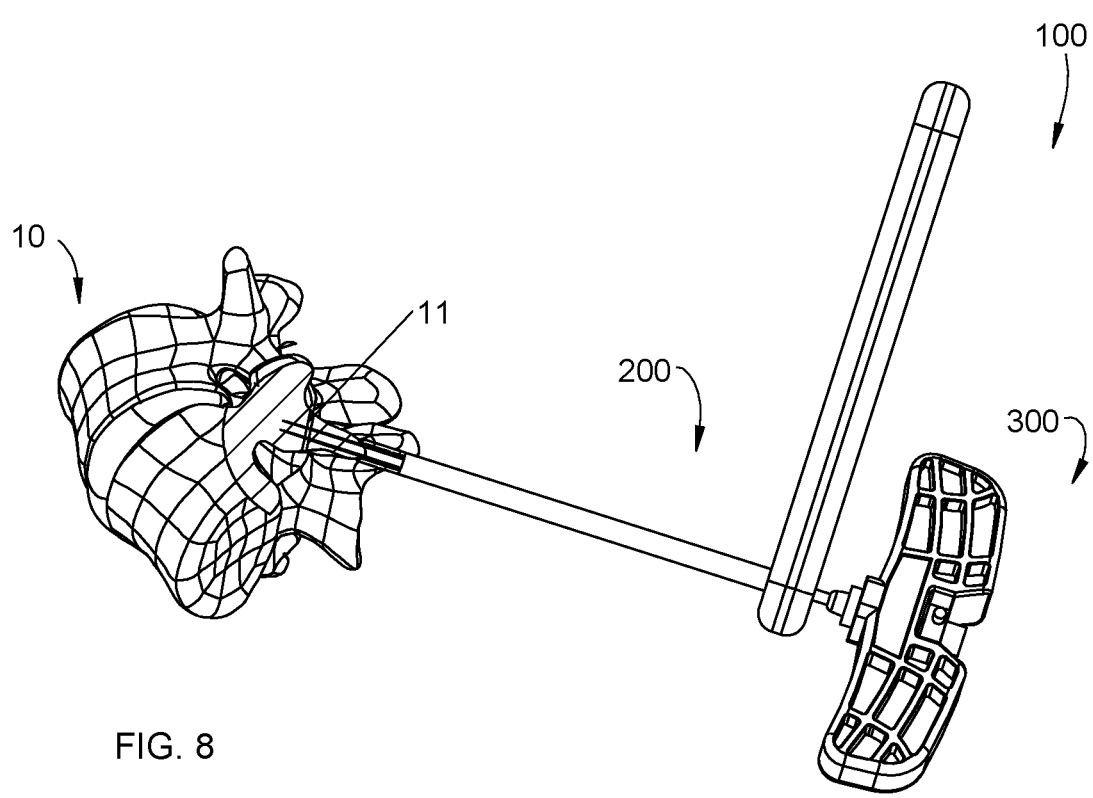

Subsequently, and with reference to FIGS. 7 and 8, stylet 400 is removed from engagement with needle assembly 300.

To remove stylet 400 from needle assembly 300, handle portion 420 of stylet 400 is pulled proximally with respect to needle assembly 300.

Figure 9:
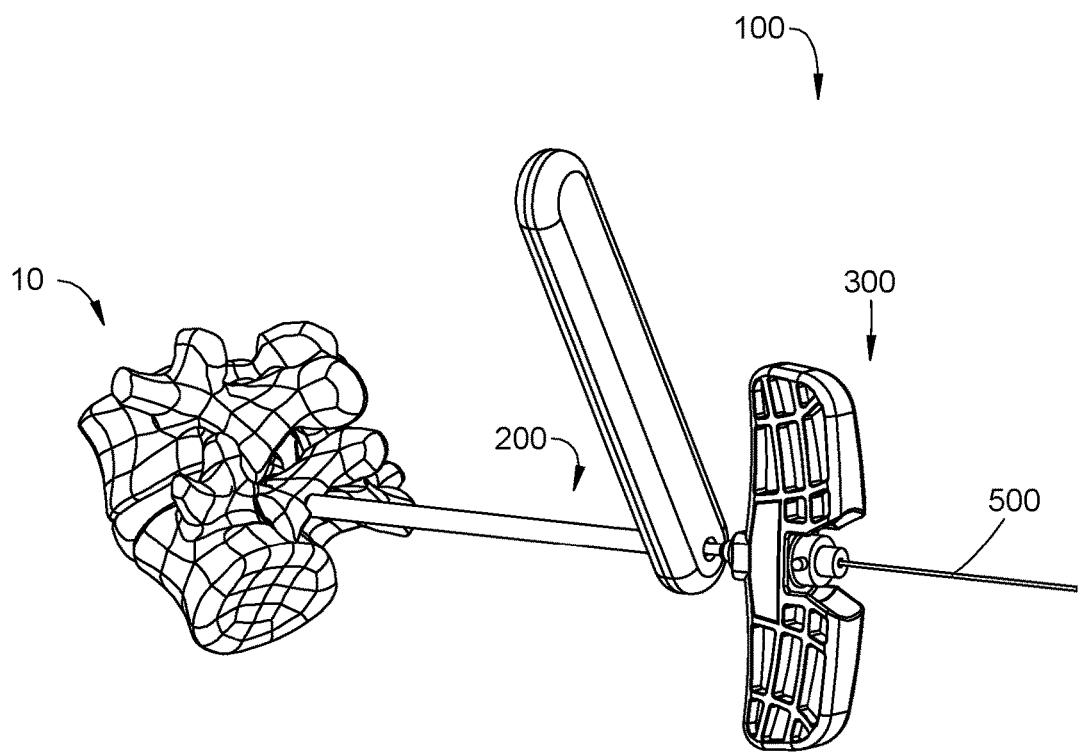
FIGS. 9 and 10 are perspective views of the needle guide shown in FIGS. 7 and 8 illustrating a guidewire inserted through the needle and needle guide.
Figure 10:
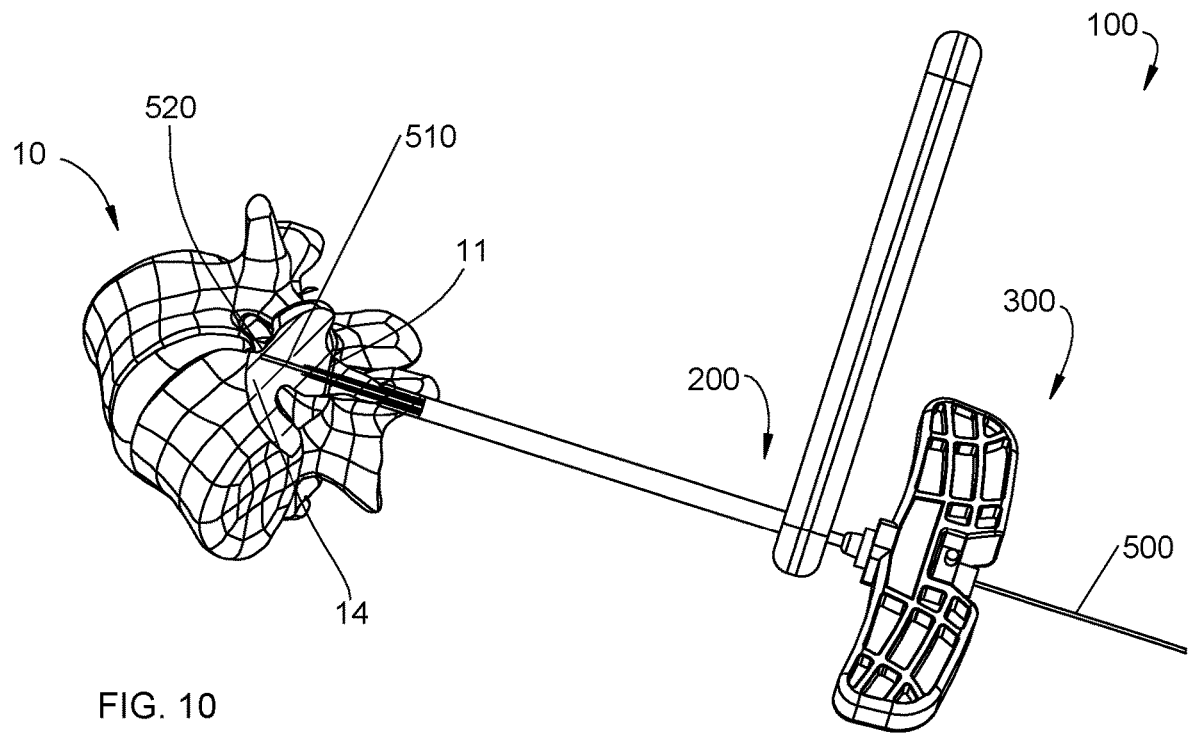

As shown in FIGS. 9 and 10, after stylet 400 is removed from engagement with needle assembly 300, guidewire 500 is inserted through passage 330 of needle assembly 300. In particular, a distal portion 510 of guidewire 500 is initially positioned adjacent handle portion 320 of needle assembly 300, and is then inserted through passage 330 of needle assembly 300 until a distal tip 520 of guidewire 500 engages (e.g., is positioned within or secured within) the lamina 14.

Figure 11:
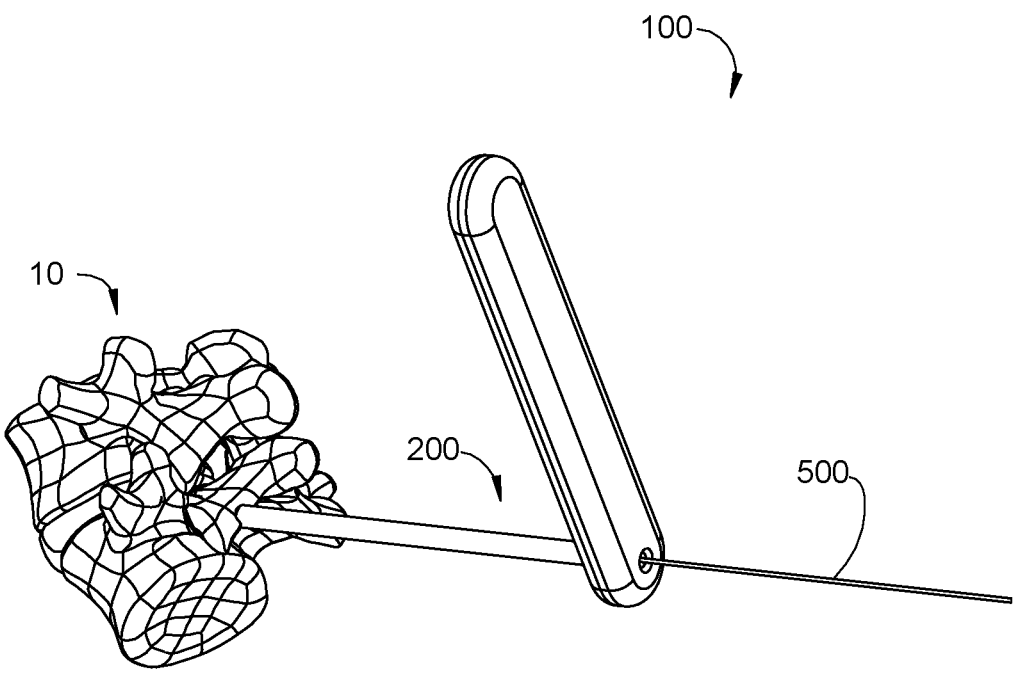
FIGS. 11 and 12 are perspective views of the needle guide shown in FIGS. 9 and 10 illustrating the guidewire through the needle guide and the needle removed from the needle guide.
Figure 12:
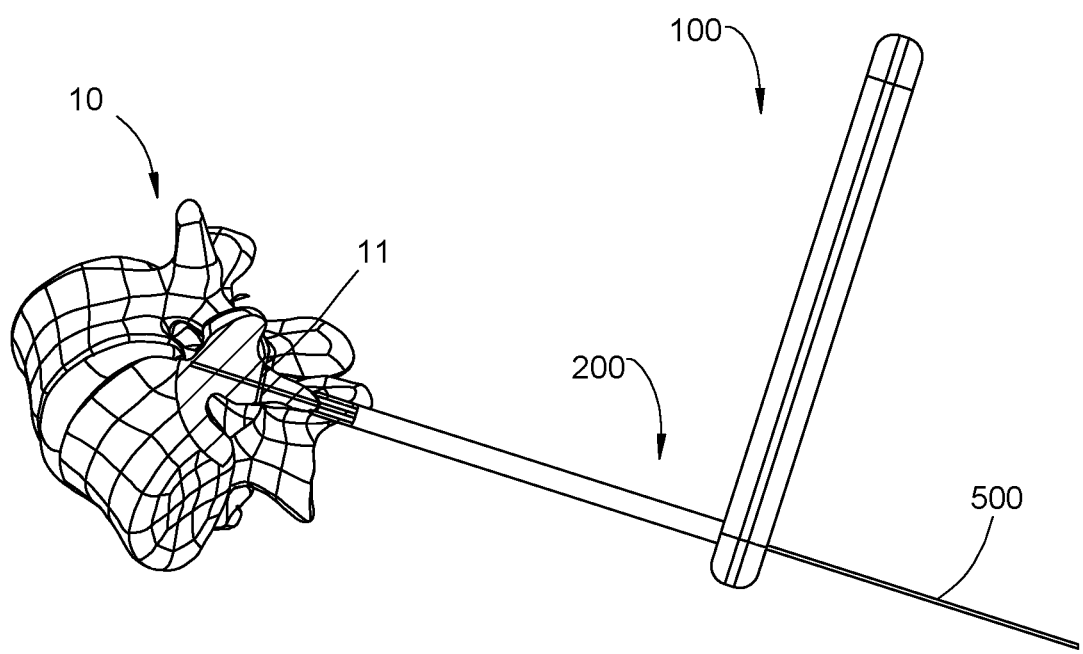
Figure 13:
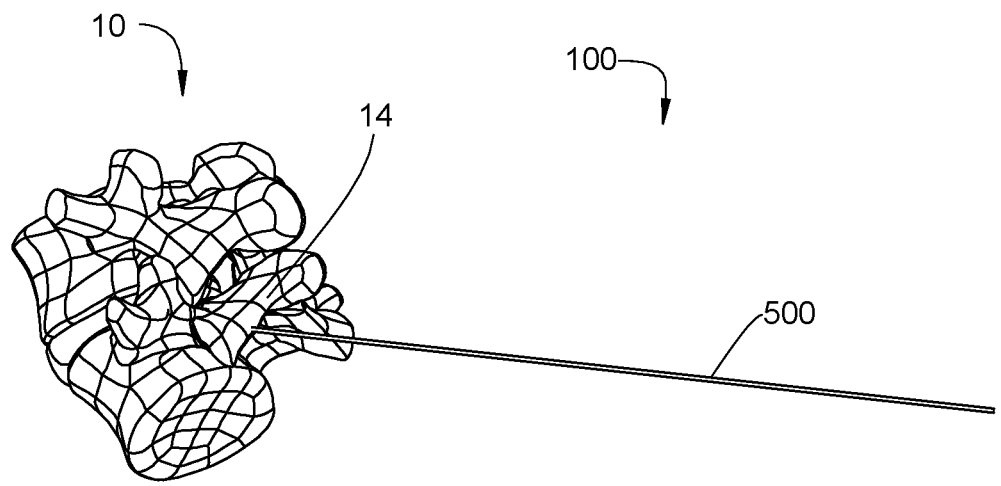
FIGS. 13 and 14 are perspective views of the guidewire shown in FIGS. 11 and 12 engaged with the fractured pars interarticularis and with the needle guide removed.
Figure 14:
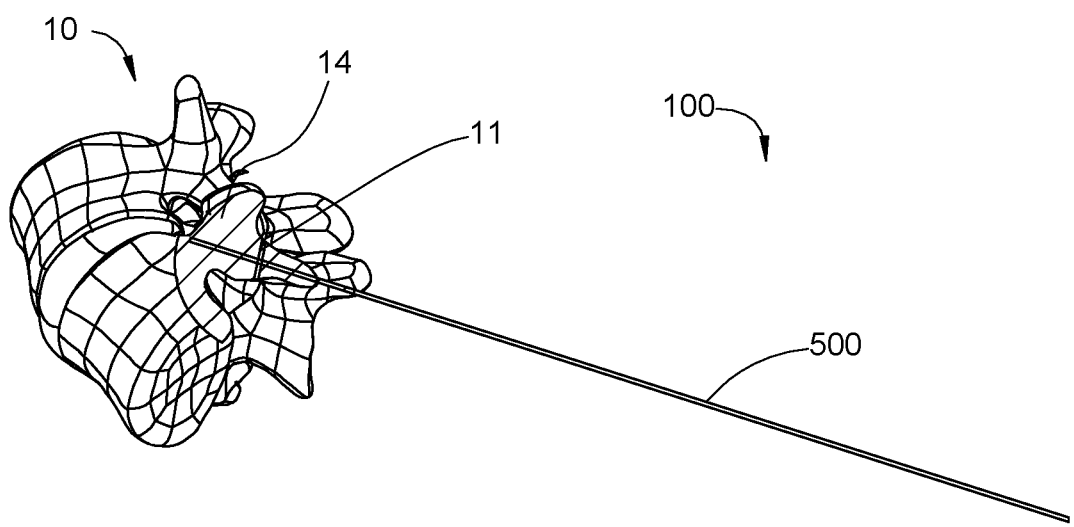

After guidewire 500 is positioned, needle assembly 300 is removed from needle guide 200 by pulling handle portion 320 of needle assembly 300 proximally relative to needle guide 200. FIGS. 11 and 12 illustrate needle assembly 300 removed from needle guide 200. Subsequently, needle guide 200 is removed by pulling needle guide 200 proximally with respect to guidewire 500. FIGS. 13 and 14 illustrate needle guide 200 removed from engagement with the lamina 14, such that only guidewire 500 is in engagement with the lamina 14.

Next, with guidewire 500 engaged with the lamina 14, a proximal side of the lamina 14 (e.g., adjacent and/or in contact with guidewire 500) may be drilled, and a reamer (not shown) may be positioned adjacent the fracture to remove scar tissue, for instance.

Figure 15:
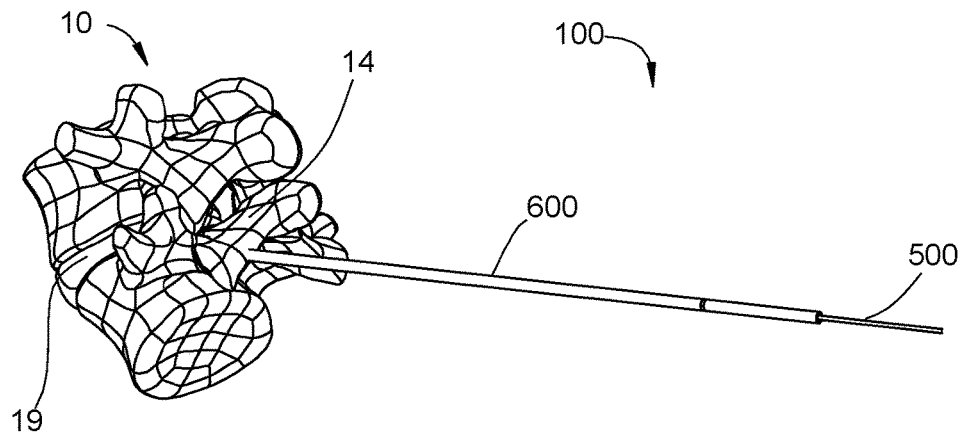
FIGS. 15 and 16 are perspective views of a screw assembly positioned over the guidewire shown in FIGS. 13 and 14 and engaged with the fractured pars interarticularis.
Figure 16:
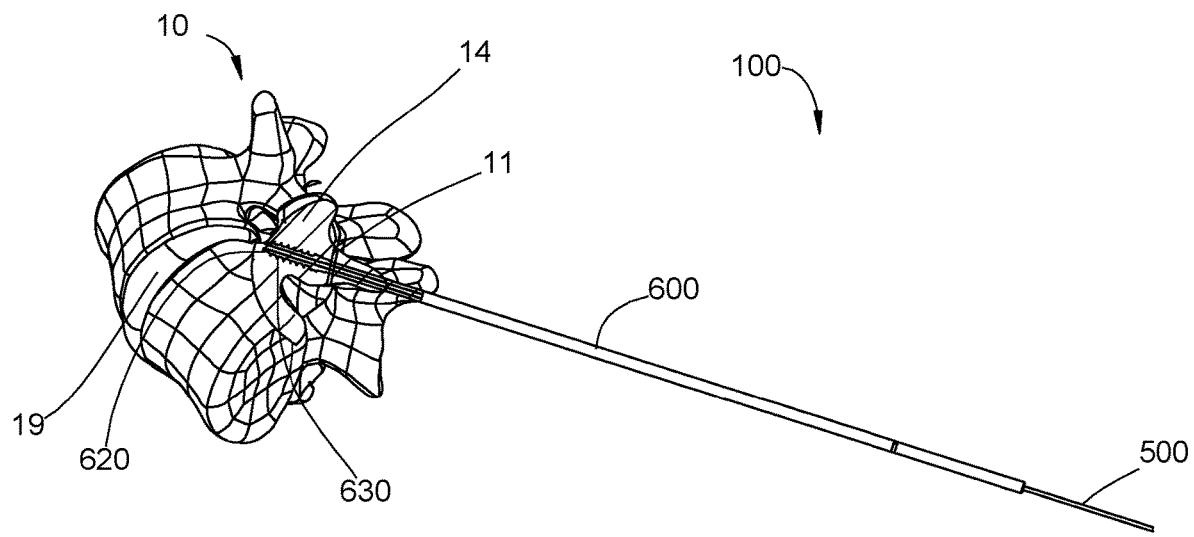
Figure 22:
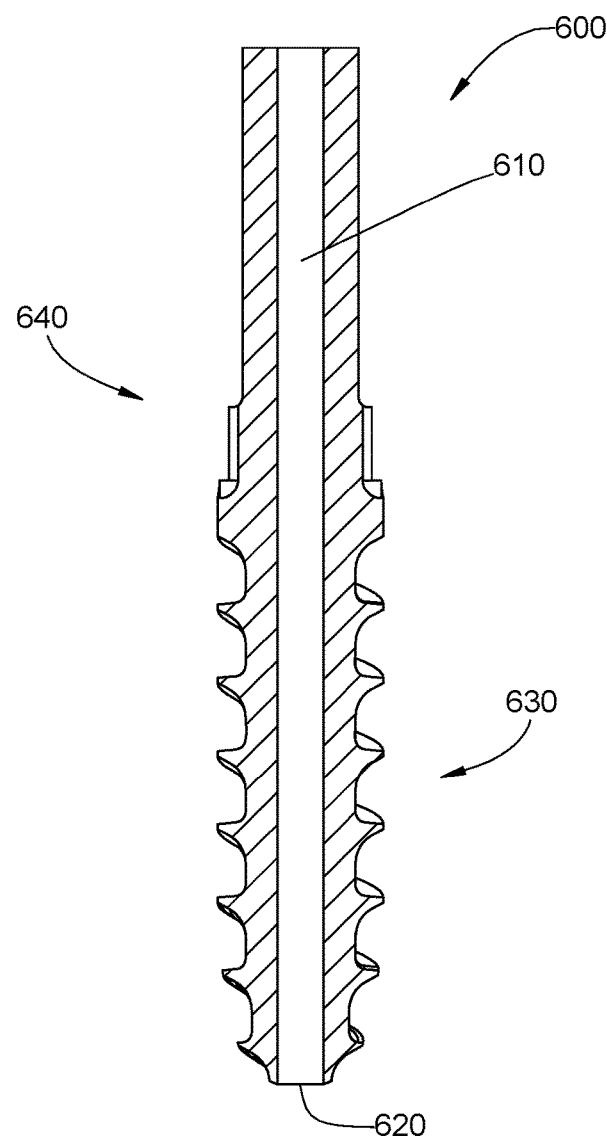
FIG. 22 is a cross-sectional view of the screw assembly of FIG. 21 taken along line 22-22.
Figure 23:
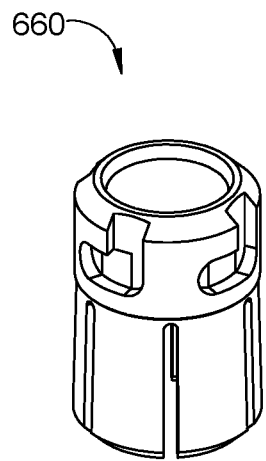
FIGS. 23-30 are perspective views of various portions of the locking cap of FIGS. 19 and 20.
Figure 24:
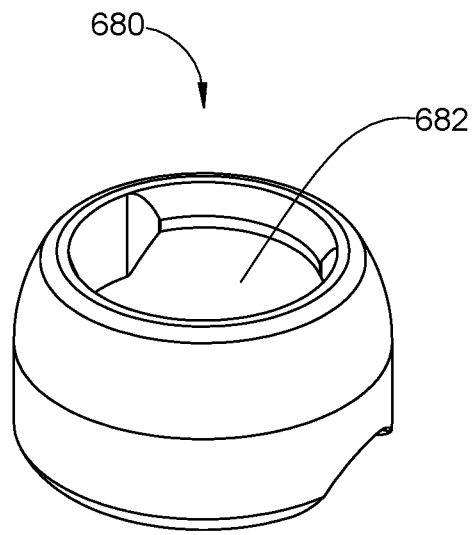
Figure 25:
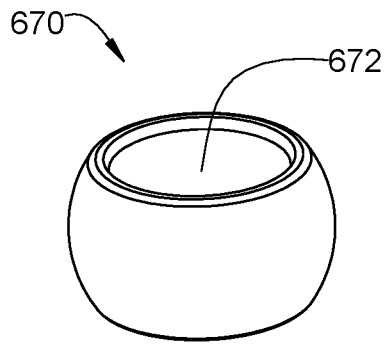
Figure 26:
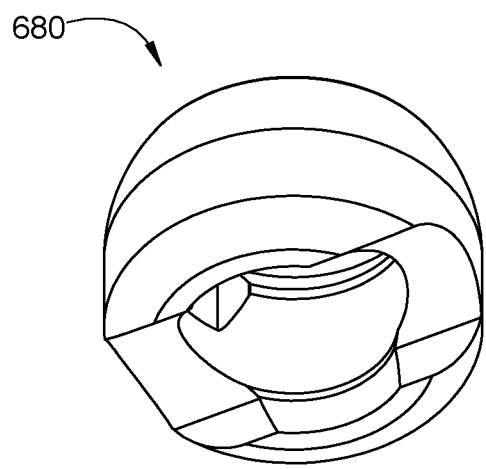

Referring now to FIGS. 15 and 16, screw assembly 600 is inserted over guidewire 500 and into contact with the lamina 14. In particular, a channel 610 of screw assembly 600 (FIG. 22) is positioned adjacent a proximal end of guidewire 500, and screw assembly 600 is moved distally such that guidewire 500 extends through channel 610 of screw assembly 600. After a distal tip 620 of screw assembly 600 engages the lamina 14, screw assembly 600 is rotated (e.g., via a hex driver) such that distal tip 620 and at least part of a threaded portion 630 of screw assembly 600 are forced distally into the lamina 14. Screw assembly 600 is rotated a sufficient amount until distal tip 620 is desirably positioned within the lamina 14 (e.g., distally adjacent the fracture 11, proximally adjacent the fracture 11, or within the fracture 11). After a portion of screw assembly 600 is positioned within the lamina 14, guidewire 500 is removed from channel 610 of screw assembly 600 by pulling guidewire 500 proximally.

Figure 17:
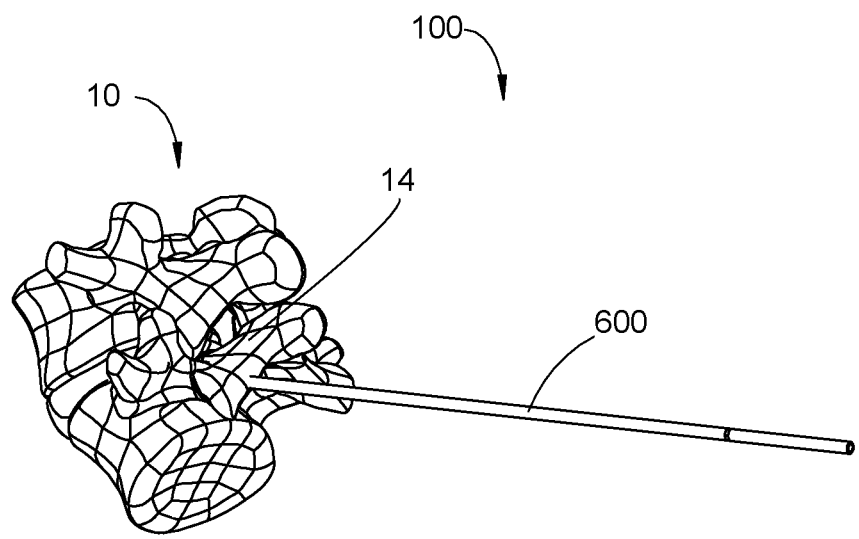
FIGS. 17 and 18 are perspective views of the screw assembly of FIGS. 15 and 16 engaged with the fractured pars interarticularis and with the guidewire removed.
Figure 18:
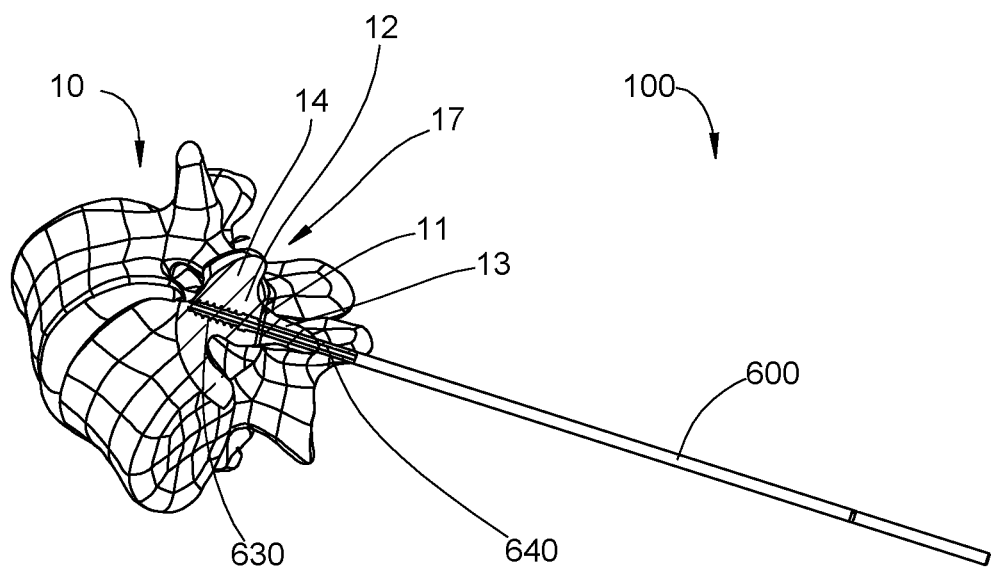

FIGS. 17 and 18 illustrate screw assembly 600 within the lamina 14 with guidewire 500 removed. As shown in FIG. 18, an elongated portion 640 of screw assembly 600 bridges the fracture 11, thus allowing the interior portion 12 of the pars 17 and the superior portion 13 of the pars 17 to be drawn or pulled together, which enables or facilitates healing of the pars 17. The pars fracture may be reamed after the screw assembly 600 has been inserted to span the pars fracture.

Figures 19, 20:
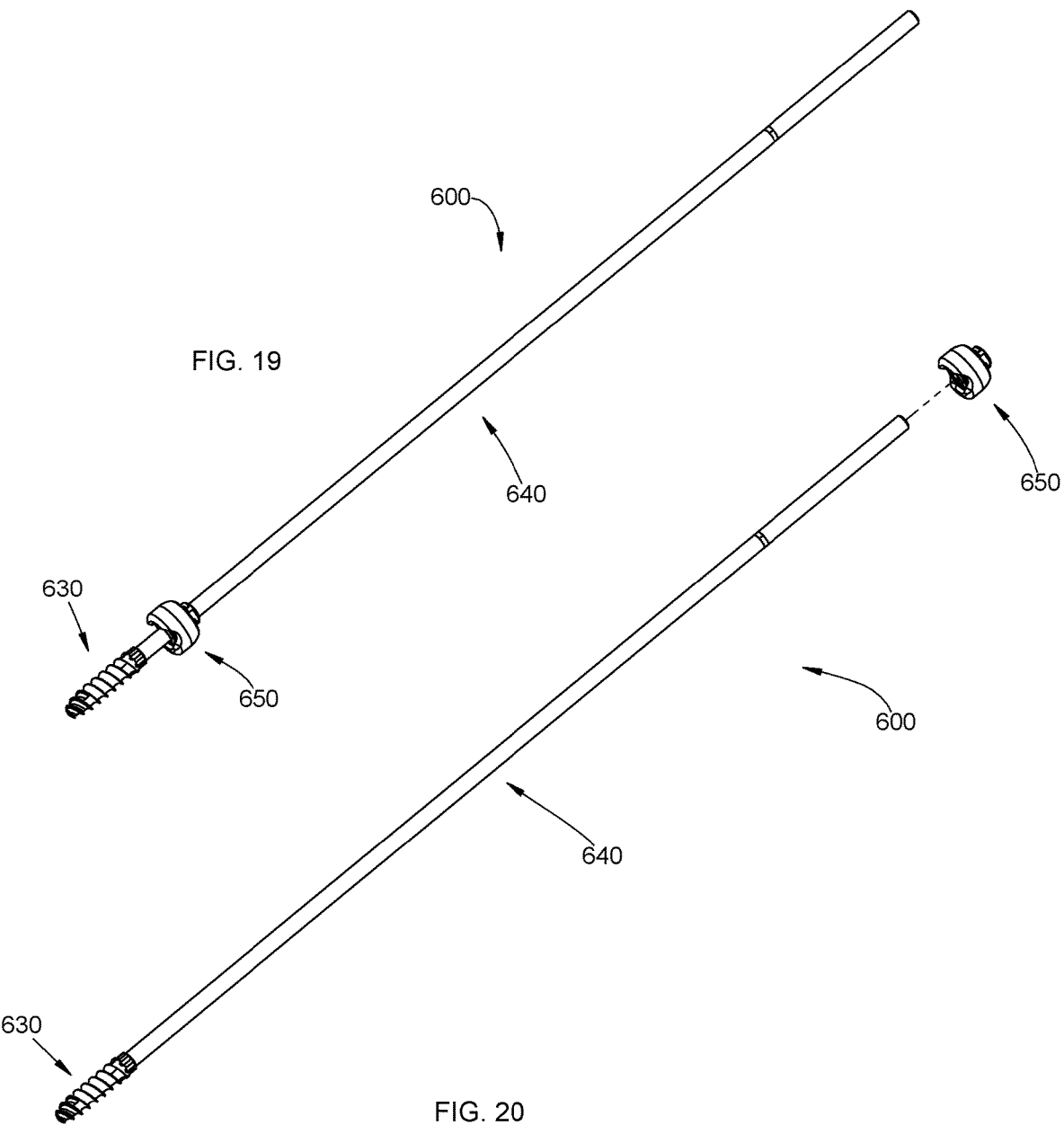
FIGS. 19 and 20 are perspective views of the screw assembly of FIGS. 15-18 with a locking cap.
Figure 21:
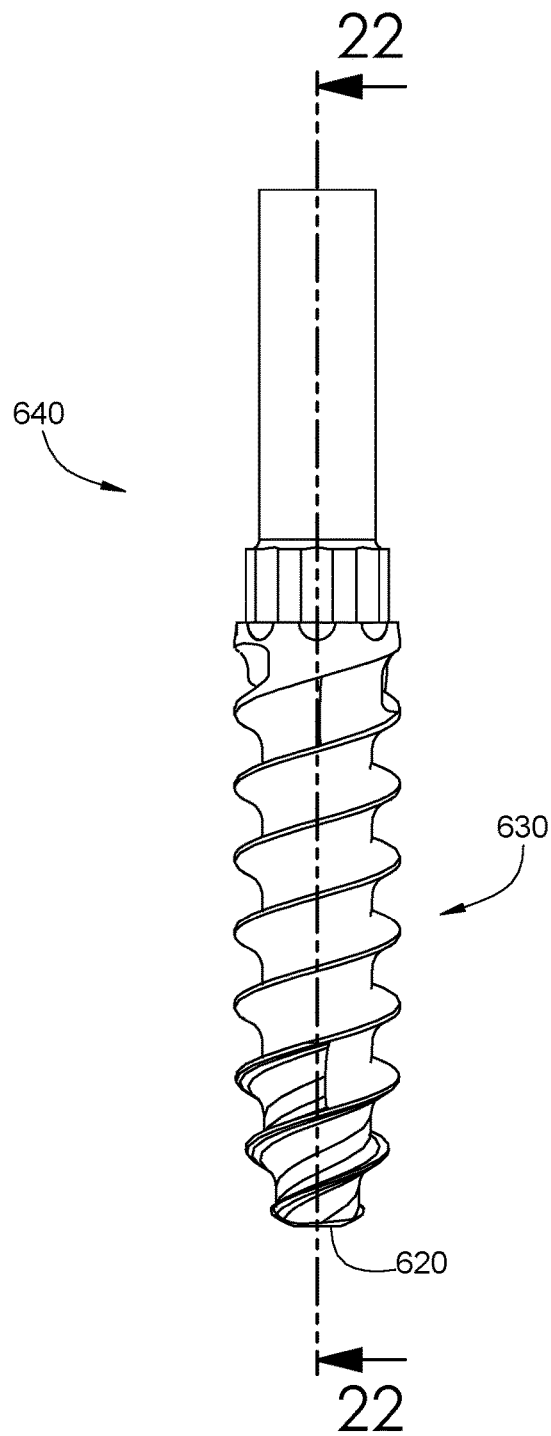
FIG. 21 is a side view of a distal portion of the screw assembly of FIGS. 15-20.
Figure 27:
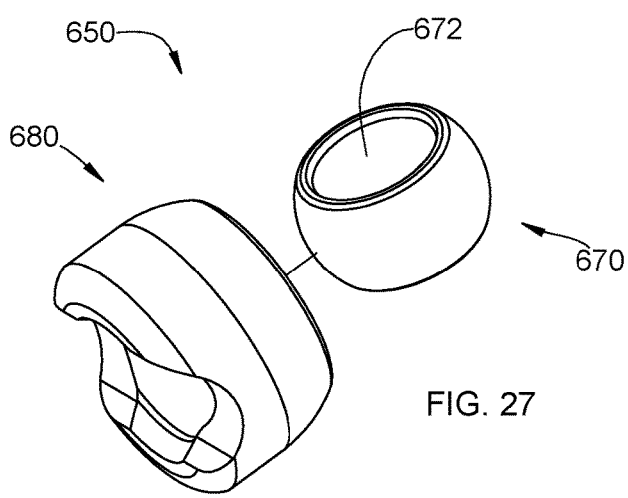
Figure 28:
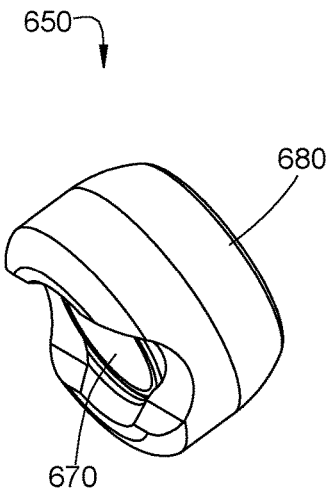
Figure 29:
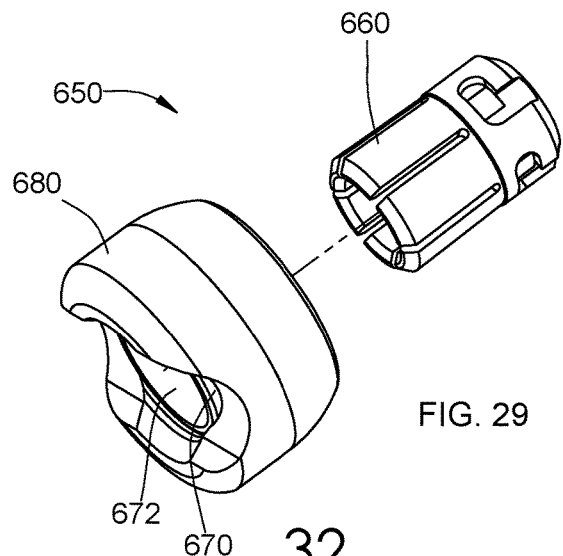
Figure 30:
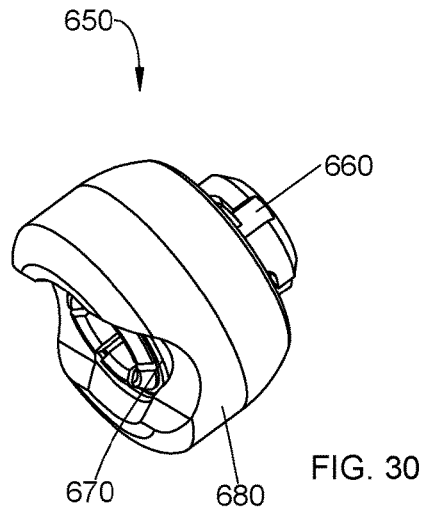
Figure 31:
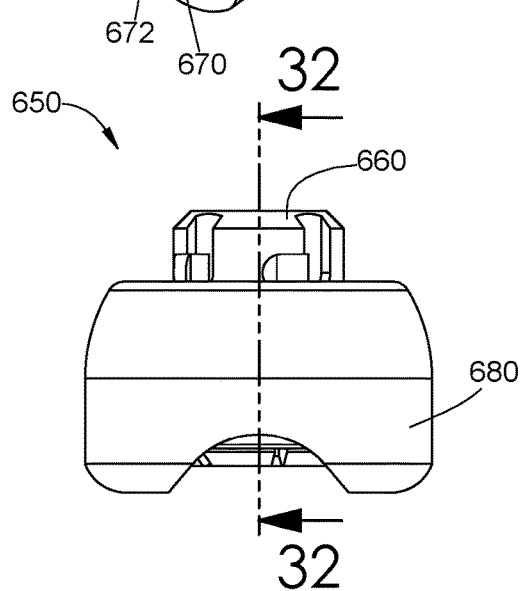
FIG. 31 is a side view of a portion of the assembled locking cap of FIGS. 23-30.
Figure 32:
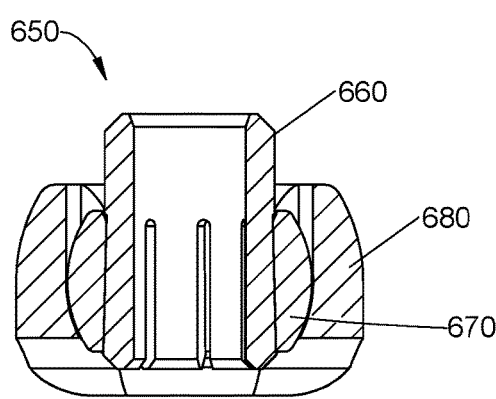
FIG. 32 is a cross-sectional view of the portion of the locking cap of FIG. 31 taken along line 32-32.

FIGS. 19-32 illustrate further details of screw assembly 600. Generally, screw assembly 600 includes elongated extension 640 and a collar assembly 650 (FIGS. 19 and 20). Threaded portion 630 is disposed on a distal end of elongated portion 640, and collar assembly 650 is slidably disposed on elongated portion 640. With particular reference to FIGS. 23-32, collar assembly 650 includes an inner sleeve 660, an annular ring 670, and an outer ring 680. Annular ring 670 is positionable within a bore 682 of outer ring 680, and is rotatable with respect to outer ring 680 (FIGS. 27 and 28). Inner sleeve 660 is positionable within a bore 672 of annular ring 670 (FIGS. 29 and 30). Additionally, while a particular type of screw head is shown, the present disclosure also contemplates different types of screw heads (e.g., including a beveled face) without departing from the scope of the present disclosure. After inserting screw assembly 600 into the lamina 14, a graft may be packed into the reamed out area of the lamina 14 adjacent screw assembly 600.

Screw assembly 600 is configured for use with a specialized surgical instrument, such as surgical instrument 700 shown in FIGS. 33-36. Screw assembly 600 and surgical instrument 700 are used to approximate the interior portion 12 of the pars 17 and the superior portion 13 of the pars 17, to thereby close the fracture 11.

Figure 33:
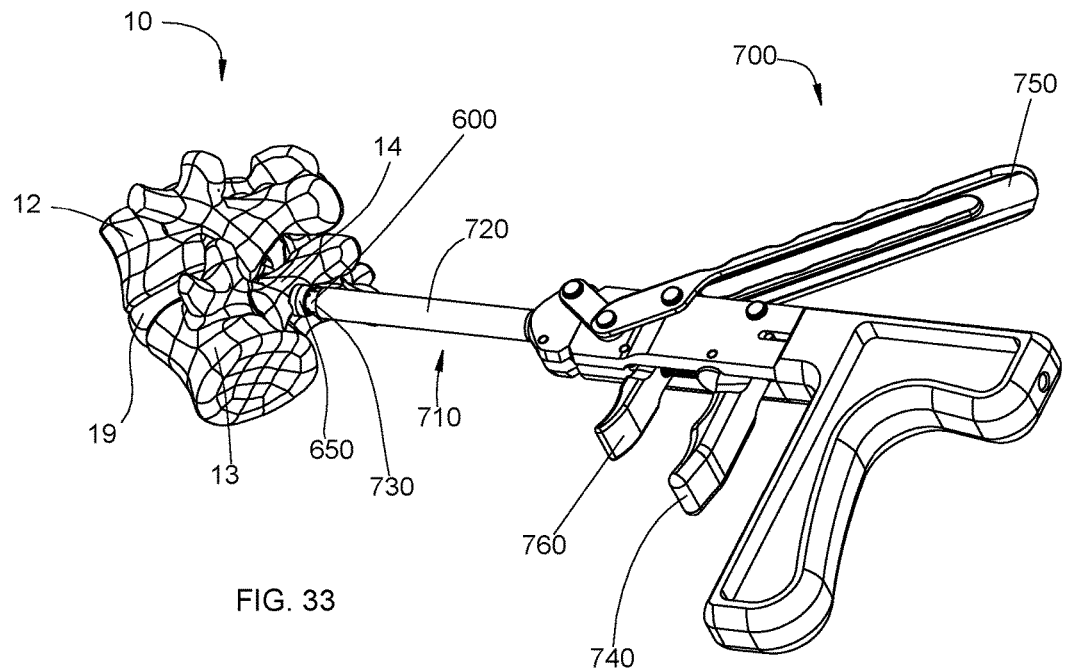
FIGS. 33-36 are perspective views of a surgical instrument engaged with the screw of FIGS. 17 and 18.
Figure 34:
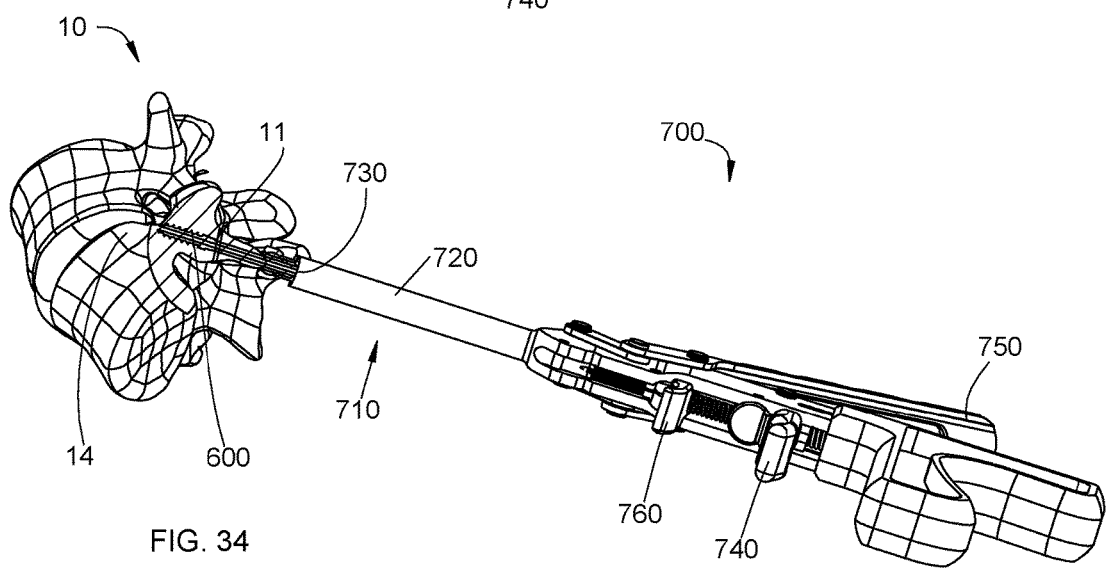
Figure 35:
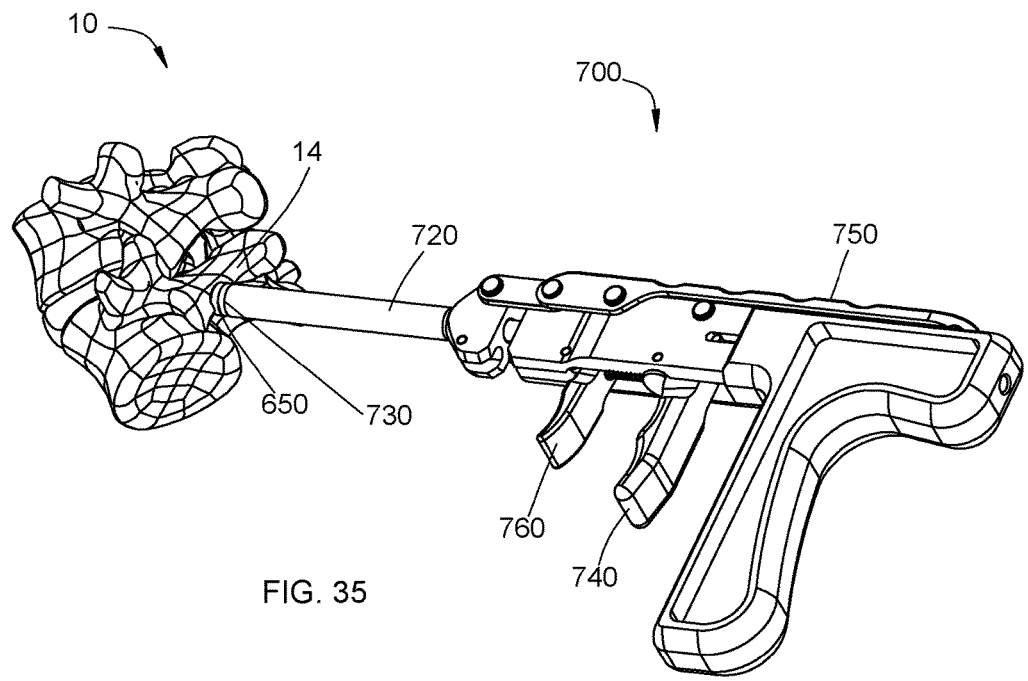
Figure 36:
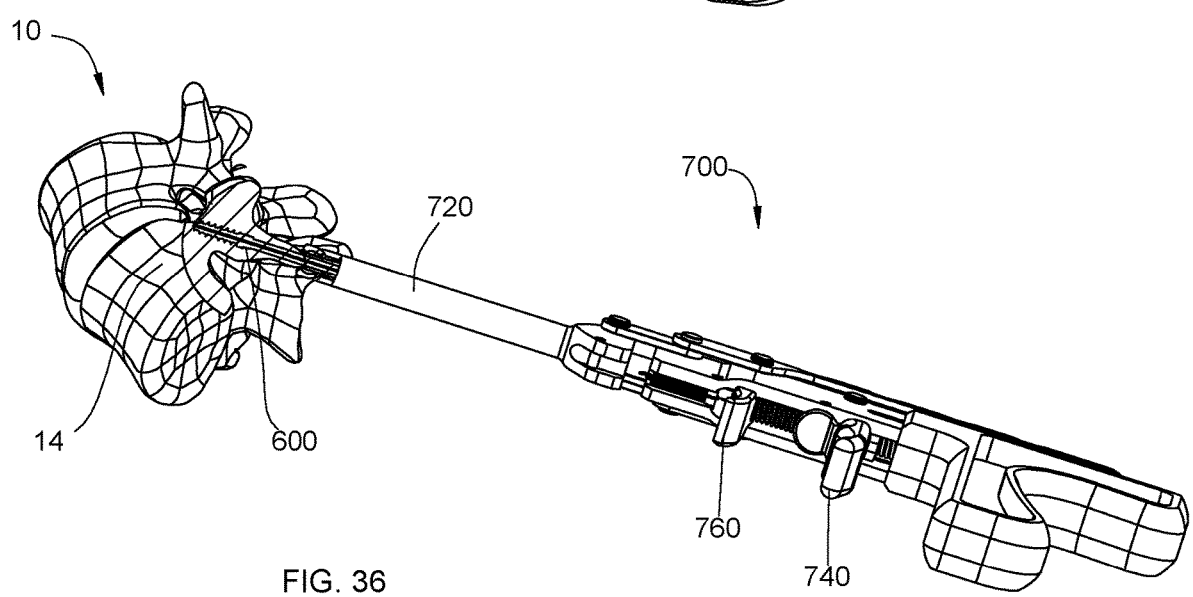
Figure 37:
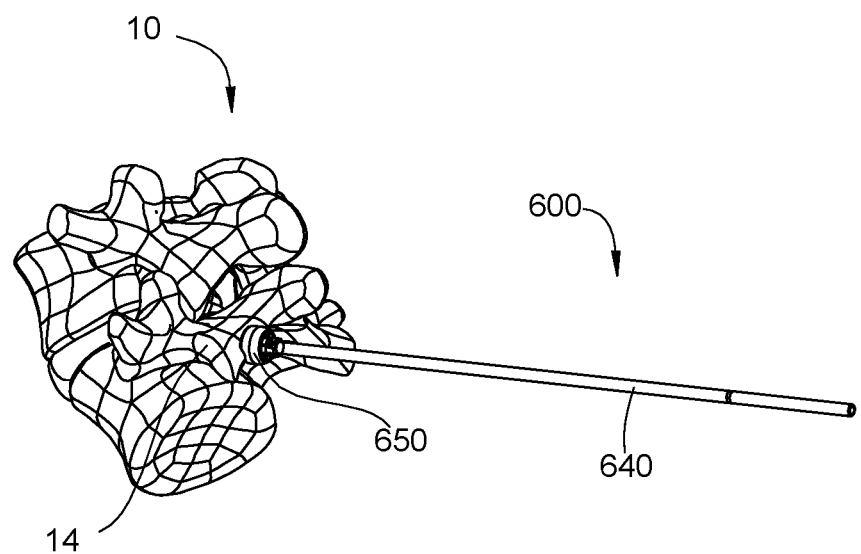
FIGS. 37 and 38 are perspective views of the screw of FIGS. 17 and 18 engaged with the pars interarticularis.
Figure 38:
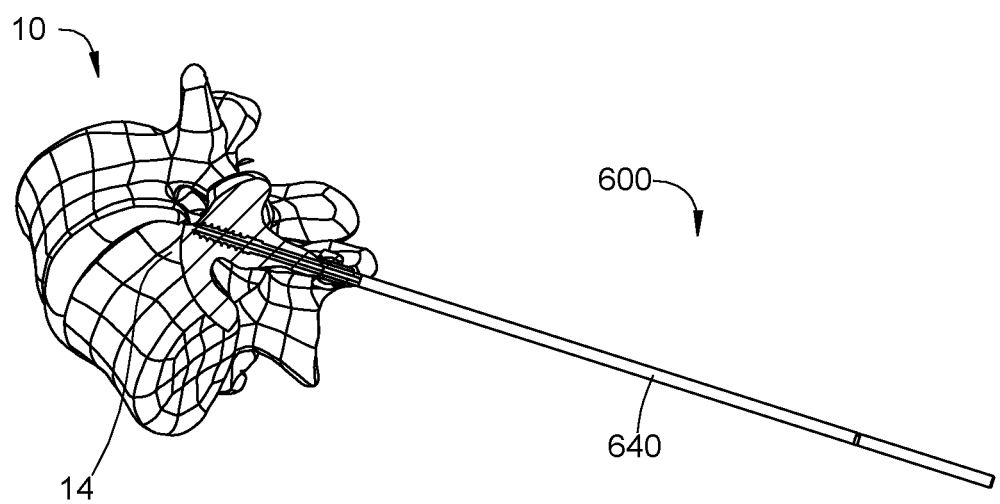

Generally, a distal portion 710 of surgical instrument 700 is positioned such that a hollow, elongated portion 720 of surgical instrument 700 radially surrounds a portion of screw assembly 600 (see FIGS. 33 and 34). In particular, a distal end 730 of surgical instrument 700 is positioned to engage collar assembly 650 of screw assembly 600 (see FIG. 35). Next, a first movable handle 740 of surgical instrument 700 is actuated which causes at least a portion of collar assembly 650 of screw assembly 600 to move distally toward threaded portion 630 of screw assembly 600, thereby approximating the interior portion 12 of the pars 17 and the superior portion 13 of the pars 17, and closing the fracture 11. The next step includes actuating a second movable handle or lever 750 of surgical instrument 700 to lock collar assembly 650 of screw assembly 600 to elongated portion 640 of screw assembly 600. In particular, actuating lever 750 causes inner sleeve 660 to be held in its position with respect to elongated portion 640, while distally advancing annular ring 670 and outer ring 680 with respect to elongated portion 640. Prior to the inner sleeve 660 engaging the elongated portion 640, the inner sleeve 660 may be moved proximally with respect to a stationary annular ring 670 and outer ring 680. This arrangement inhibits the surgical instrument 700 from over compressing the pars fracture during approximation, or locking. A third movable handle 760 of surgical instrument 700 is then actuated to release surgical instrument 700 from engagement with screw assembly 600, while collar assembly 650 remains secured in place with respect to elongated portion 640 of screw assembly 600

Figure 39:
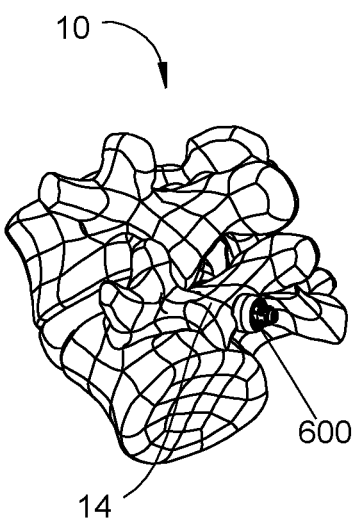
FIGS. 39 and 40 are perspective views of the screw assembly of FIGS. 19 and 20 engaged with the pars interarticularis and with the elongated portion of the screw assembly removed.
Figure 40:
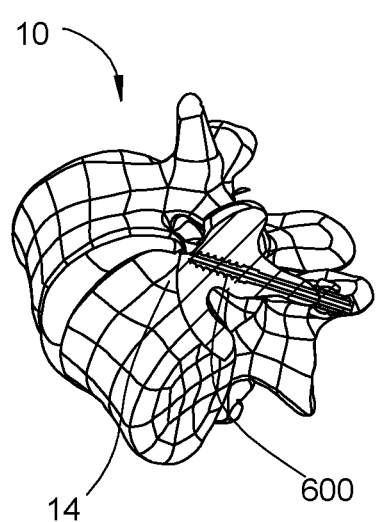

With reference to FIGS. 37-40, after surgical instrument 700 is removed from engagement with screw assembly 600 (FIGS. 37 and 38), a user cuts off the part of elongated portion 640 of screw assembly 600 that protrudes from the lamina 14 (e.g., the portion disposed proximally of collar assembly 650; FIGS. 39 and 40). It is envisioned that a separate tool or instrument (e.g., a shearing rod cutter-type instrument) is used to cut screw assembly 600. It is also envisioned that screw assembly 600 includes a frangible portion (e.g., at or near the proximal end of threaded portion 630) configured to facilitate the severing of part of elongated portion 640 of screw assembly 600 after the surgical procedure is complete.

Accordingly, the use of fixation system 100 enables the repair of a pars fracture using a single-incision, minimally-invasive procedure.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described.

What is claimed is:

1. A method of repairing a pars fracture, comprising:
docking a needle guide on a lamina of the pars;
inserting a needle at least partially through the needle guide such that a distal end of the needle contacts the lamina;
inserting a stylet at least partially through the needle such that a distal end of the stylet contacts the lamina;
inserting a guidewire at least partially through the needle such that a distal end of the guidewire contacts the lamina;
removing the needle from the needle guide;
removing the needle guide;
positioning a screw assembly in contact with the lamina and co-axially with the guidewire;
rotating an elongated portion of the screw assembly with respect to the lamina to move the screw assembly distally with respect to the lamina such that a distal end of the elongated portion of the screw assembly travels through an interior portion of the pars and into a superior portion of the pars;
approximating the distal end of the elongated portion of the screw assembly and a collar assembly of the screw assembly to approximate the interior portion of the pars and the superior portion of the pars;
engaging a surgical instrument with the screw assembly prior to approximating the distal end of the elongated portion of the screw assembly and the collar assembly of the screw assembly;
actuating a first movable handle of the surgical instrument to approximate the distal end of the elongated portion of the screw assembly and the collar assembly of the screw assembly; and
actuating a second movable handle of the surgical instrument to fix a longitudinal position of the collar assembly of the screw assembly with respect to the elongated portion of the screw assembly.

2. The method according to claim 1, further comprising removing the guidewire through a channel of the elongated portion of the screw assembly.

3. The method according to claim 1, wherein inserting the needle and inserting the stylet are performed at the same time.

4. The method according to claim 1, further comprising severing a portion of the screw assembly after approximating the distal end of the elongated portion of the screw assembly and the collar assembly of the screw assembly.

5. The method of claim 4, wherein the elongated portion includes a frangible portion and severing the portion of the screw assembly includes severing the frangible portion.

6. The method according to claim 1, further comprising removing the stylet from the needle.

7. The method of claim 1, further comprising locking the collar assembly to the elongated portion by fixing a longitudinal position of a first portion of the collar assembly to the elongated portion and moving a second portion of the collar assembly with respect to the first portion, the first portion including a body and a plurality of legs extending from the body.

8. The method of claim 7, wherein locking the collar assembly includes the second portion of the collar assembly applying a pressure to the plurality of legs.

9. The method of claim 7, wherein locking the collar assembly includes moving a third portion of the collar assembly with respect to the first portion of the collar assembly.

10. The method of claim 9, wherein locking the collar assembly includes simultaneously moving the second portion and the third portion.

* * * * *